(12) United States Patent
Cunningham et al.

(10) Patent No.: US 9,400,353 B2
(45) Date of Patent: Jul. 26, 2016

(54) SILICON-BASED PHOTONIC CRYSTAL FLUORESCENCE ENHANCEMENT AND LASER LINE SCANNING INSTRUMENT

(71) Applicant: The Board of Trustees of the University of Illinois, Urbana, IL (US)

(72) Inventors: Brian T. Cunningham, Champaign, IL (US); Sherine George, Hillsboro, OR (US); Anusha Pokhriyal, Mountain View, CA (US); Vikram Chaudhery, Springfield, IL (US); Meng Lu, Ames, IA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 421 days.

(21) Appl. No.: 13/961,697

(22) Filed: Aug. 7, 2013

(65) Prior Publication Data

US 2014/0323323 A1    Oct. 30, 2014

Related U.S. Application Data

(60) Provisional application No. 61/817,773, filed on Apr. 30, 2013.

(51) Int. Cl.
| | |
|---|---|
| *G02B 6/12* | (2006.01) |
| *G01N 21/64* | (2006.01) |
| *G02B 6/122* | (2006.01) |
| *G01N 21/77* | (2006.01) |

(52) U.S. Cl.
CPC ............... *G02B 6/12* (2013.01); *G01N 21/648* (2013.01); *G02B 6/1225* (2013.01); *G01N 21/7743* (2013.01)

(58) Field of Classification Search
USPC ............................................. 385/14
See application file for complete search history.

(56) References Cited

U.S. PATENT DOCUMENTS

| | | | | |
|---|---|---|---|---|
| 6,611,636 B2* | 8/2003 | Deliwala | ............... | B82Y 20/00 |
| | | | | 257/E27.112 |
| 7,479,404 B2* | 1/2009 | Cunningham | ......... | B82Y 20/00 |
| | | | | 438/32 |
| 7,768,640 B2 | 8/2010 | Cunningham et al. | | |

(Continued)

OTHER PUBLICATIONS

International Search Report and Written Opinion of International Application No. PCT/US2014/032659, mailed Oct. 8, 2014.

(Continued)

*Primary Examiner* — Eric Wong
(74) *Attorney, Agent, or Firm* — McDonnell Boehnen Hulbert & Berghoff LLP

(57) ABSTRACT

A silicon-based photonic crystal includes a silicon substrate, a first dielectric with a grating structure formed therein, and a second dielectric with a higher index of refraction that covers at least a portion of the grating structure. The first dielectric can be formed on the silicon substrate, or a Fabry-Perot optical cavity can be formed between the silicon substrate and the first dielectric. An instrument can excite a fluorophore coupled to the photonic crystal by focusing collimated incident light that includes the fluorophore's excitation wavelength to a focal line on the surface of the photonic crystal such that the focal line is substantially parallel to the grating direction and can detect fluorescence radiation emitted by the fluorophore in response to the incident light. To provide for fluorescence enhancement, the excitation wavelength and/or emission wavelength of the fluorophore can couple to an optical resonance of the photonic crystal.

26 Claims, 9 Drawing Sheets

(56) References Cited

U.S. PATENT DOCUMENTS

| | | |
|---|---|---|
| 7,961,315 B2 | 6/2011 | Cunningham et al. |
| 2012/0000700 A1* | 1/2012 | Liu .................. G01N 21/64 21/64 |
| 2012/0007000 A1 | 1/2012 | Lu et al. |
| 2013/0121633 A1* | 5/2013 | Painter ................. G02B 26/001 385/14 |

OTHER PUBLICATIONS

Pokhriyal et al., "Photonic crystal enhanced fluorescence using a quartz substrate to reduce limits of detection", Optics Express, Nov. 22, 2010, vol. 18, pp. 24793-24808.

Chaudhery et al., "Angle-Scanning Photonic Crystal Enhanced Fluorescence Microscopy", Journal Sensors IEEE, 2012, vol. 12, pp. 1272-1279.

Estrada et al., "Small volume excitation and enhancement of dye fluorescence on a 2D photonic crystal surface", Optics Express, Feb. 15, 2010, vol. 18, pp. 3693-3699.

Zhu et al., "Analysis of yeast protein kinases using protein chips", Nature Genetics, Nov. 2000, vol. 26, pp. 283-290.

Park et al., "High-resolution electrohydrodynamic jet printing", Nature Materials, Oct. 2007, vol. 6, pp. 782-789.

Park et al., "Nanoscale Patterns of Oligonucleotides Formed by Electrohydrodynamic Jet Printing with Applications in Biosensing and Nanomaterials Assembly", Nano letters, Oct. 2008, vol. 8, pp. 4210-4216.

Block et al., "A detection instrument for enhanced-fluorescence and label-free imaging on photonic crystal surfaces", Optics Express, Jul. 20, 2009, vol. 17, pp. 13222-13235.

Chaudhery et al., "Line-scanning detection instrument for photonic crystal enhanced fluorescence", Optics Letters, Jul. 1, 2012, vol. 37, pp. 2565-2567.

George et al., "Label-Free Prehybridization DNA Microarray Imaging Using Photonic Crystals for Quantitative Spot Quality Analysis", Analytical Chemistry, 2010, vol. 82, pp. 8551-8557.

* cited by examiner

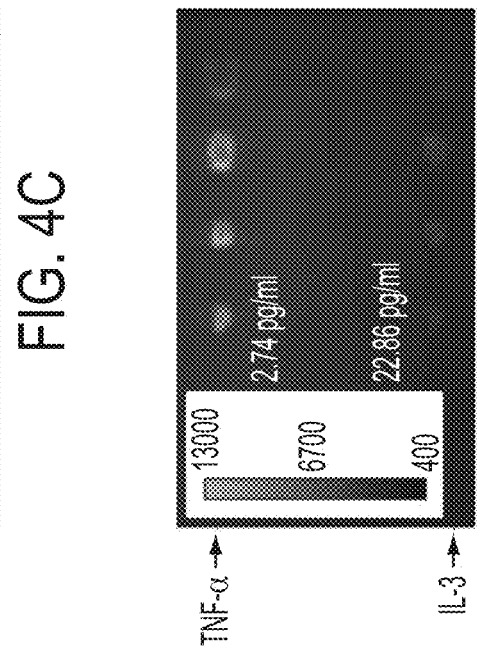
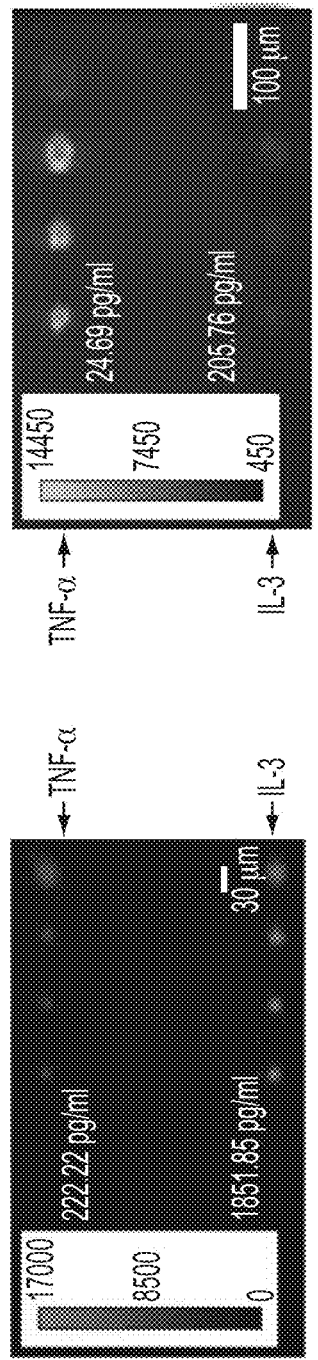
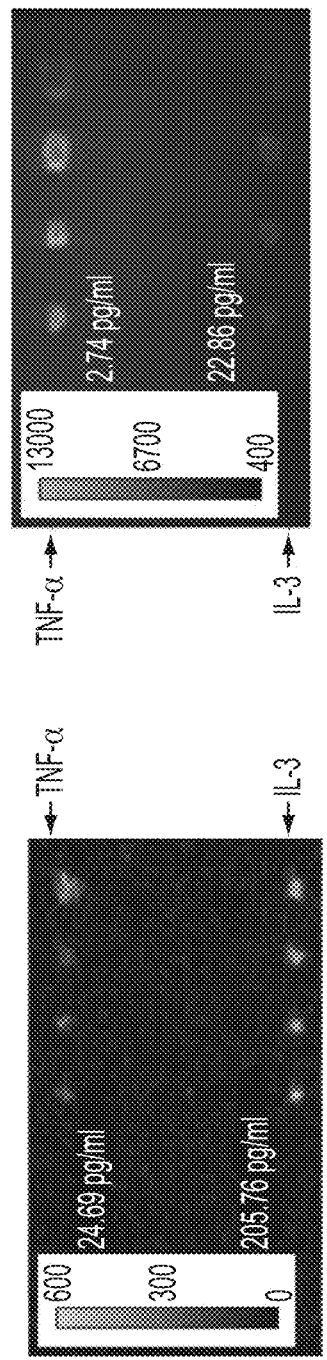
FIG. 4A  FIG. 4B  FIG. 4C  FIG. 4D

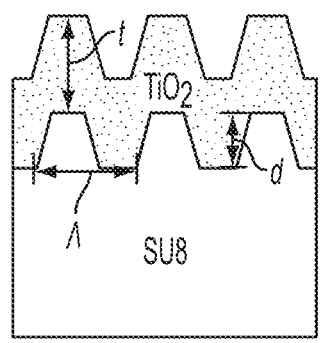
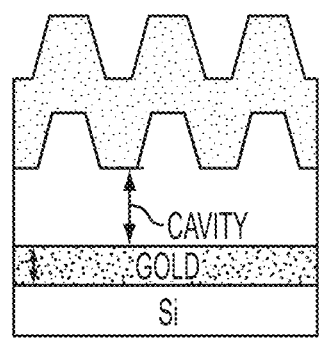
FIG. 7A          FIG. 7B
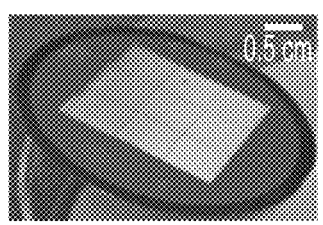
FIG. 7C          FIG. 7D

SILICON-BASED PHOTONIC CRYSTAL FLUORESCENCE ENHANCEMENT AND LASER LINE SCANNING INSTRUMENT

PRIORITY

This application claims priority under 35 U.S.C. §119(e) to U.S. Provisional Application No. 61/817,773 filed Apr. 30, 2013, the content of which is incorporated herein by reference.

GRANT FUNDING

This invention was made with government support under Grant No. PHS 1R01 GM086382 A, awarded by the National Institutes of Health, and Grant No. CBET 07-54122, awarded by the National Science Foundation. The government has certain rights in the invention.

BACKGROUND

Circulating blood contains a diverse set of cellular and molecular elements that can be detected and quantified to indicate the presence of cancers, allergies, heart disease, and neurodegenerative disease. The detection of bloodborne biomarkers has value not only for disease detection, but also for informing the prescription choice for personalized therapies and in the monitoring of these treatments. For example, biomarker levels can help assist the development of novel molecular-targeted therapeutic strategies, identify patients who are likely to benefit from a specific targeted treatment, as well as provide molecular endpoints to predict and monitor treatment efficacy.

In the most general sense, a biomarker is any measurable factor that differentiates a normal biological process from a disease-related process or its response to therapy. In the search for cancer biomarkers, the quantitative analysis of products of cancer cells, the tumor microenvironment, the host's response, and the interaction between these three components has yielded several potential candidates. Circulating protein markers are currently in clinical use for the diagnoses of ovarian, pancreatic, colon, and prostate cancers. Exosomal microRNAs (miRNA), which are 18-24 bases long double stranded noncoding RNA that regulate expression through control over mRNA and protein translation, is another class of biomarker molecules that has been keenly studied as their expression is altered in disease states, notably in cancers. A special consideration for detecting cancer biomarkers is that tumors initially develop from a small population of defective cells, and hence it is highly desirable to be able to detect the presence of the smallest number of tumor cells (i.e. early intervention) when a patient's clinical outcomes and prognosis are still favorable. Although reports of several bioanalytical techniques for cancer biomarker detection exist, an unmet, critical limitation is the reliable and accurate detection of cancer biomarkers mainly due to (a) insufficient sensitivity of the assay and (b) insufficient dynamic range needed to detect biomarkers anywhere from the low ng/mL to the low pg/mL range.

To maximize the applicability and accessibility of a biomarker detection platform, the ability to perform sensing non-invasively is highly desirable, particularly if it can utilize a sample comprised of a single droplet of blood. The adoption of biomarker tests may be accelerated by methods that can be performed with minimal sample preparation and technical expertise, potentially enabling testing to be performed in close proximity to the patient. Such a portable platform would help reduce costs, minimize sample degradation, provide on-spot diagnosis thus alleviating patient stress, and finally guide the course therapy especially when timely adjustments in treatment are critical. It is further desirable for detection instruments used in a point-of-care setting to be inexpensive, compact, and rugged.

SUMMARY

In one aspect, example embodiments provide a photonic crystal structure comprising a silicon substrate, a first dielectric, and a second dielectric. The first dielectric has a first index of refraction and has a first surface facing the silicon substrate and a second surface opposite the first surface. The second surface has a grating structure formed therein. The second dielectric has a second index of refraction that is higher than the first index of refraction. The second dielectric covers at least a portion of the grating structure such that the first and second dielectrics together define a photonic crystal having an optical resonance.

In some examples, the first dielectric comprises silicon oxide and the second dielectric comprises titanium oxide.

The first surface of the first dielectric could be in contact with the silicon substrate. Alternatively, the photonic crystal structure could include one or more intermediate layers between the silicon substrate and the first dielectric. The one or more layers may define a Fabry-Perot optical cavity. For example, the one or more intermediate layers could include a reflective metal layer (e.g., gold) on the silicon substrate and a spacer layer that provides a defined spacing between the metal layer and first dielectric. The defined spacing could be chosen such that the Fabry-Perot optical cavity couples to the optical resonance of the photonic crystal.

In some examples, a fluorophore may be coupled to a surface of the photonic crystal. The fluorophore is configured to emit fluorescence radiation at an emission wavelength (the fluorescence radiation may occur at an emission angle relative to a normal to the surface of the photonic crystal) in response to receiving excitation radiation at an excitation wavelength (the excitation radiation may be incident at an excitation angle relative to the normal to the surface of the photonic crystal). In some examples, the optical resonance of the photonic crystal has a resonance wavelength at the excitation angle that corresponds to the excitation wavelength of the fluorophore. In some examples, the optical resonance of the photonic crystal has a resonance wavelength at the emission angle that corresponds to the emission wavelength of the fluorophore. In some examples, the excitation wavelength, excitation angle, emission wavelength, and emission angle may be such that both the excitation radiation and emission radiation couple to the optical resonance of the photonic crystal.

In another aspect, example embodiments provide a method in which a functionalized photonic crystal structure is exposed to a sample to provide a sample-exposed photonic crystal structure. The functionalized photonic crystal structure comprises a silicon substrate, a photonic crystal having an optical resonance, and a capture ligand coupled to a surface of the photonic crystal. The capture ligand is configure to bind to a target in the sample to form a fluorescent complex, wherein the fluorescent complex includes a fluorophore that is configured to emit fluorescence radiation at an emission wavelength in response to receiving excitation radiation at an excitation wavelength. The sample-exposed photonic crystal structure is exposed to incident light from a light source at an angle of incidence. The incident light includes light at the excitation wavelength. A detector detects fluorescence radiation emitted from the fluorescent complex at an emission angle in response to the incident light from the light source.

The fluorophore could be present in the functionalized crystal structure prior to exposing the functionalized photonic crystal structure to the sample, or the fluorophore could be present in the sample prior to exposing the functionalized photonic crystal structure to the sample.

The capture ligand could be, for example, an antibody or an oligonucleotide that is specific to the target. In some examples, a plurality of different capture ligands are bound to the surface of the photonic crystal at a plurality of discrete locations such that each capture ligand is configured to bind to a respective target in the sample to form a respective fluorescent complex. In such examples, each discrete location in the sample-exposed photonic crystal structure can be sequentially exposed to incident light from the light source at the angle of incidence, and the detector may sequentially detect fluorescence radiation emitted at the emission angle from each respective fluorescent complex in each discrete location.

In some examples, the optical resonance of the photonic crystal has a resonance wavelength at the angle of incidence that corresponds to the excitation wavelength of the fluorophore. In some examples, the optical resonance of the photonic crystal has a resonance wavelength at the emission angle that corresponds to the emission wavelength of the fluorophore. In some examples, the excitation wavelength, angle of incidence, emission wavelength, and emission angle may be such that both the excitation radiation and emission radiation couple to the optical resonance of the photonic crystal.

In some examples, the photonic crystal comprises a grating structure having a grating direction, and the incidence light from the light source is focused to a focal line on the surface of the photonic crystal such that the focal line is substantially parallel to the grating direction. In such examples, the light from the light source can be collimated at the focal line in a direction substantially perpendicular to the grating direction.

In another aspect, example embodiments provide an instrument that can be used to excite a fluorophore coupled to a surface of a photonic crystal. The photonic crystal has an optical resonance and comprises a grating structure having a grating direction. The fluorophore is configured to emit fluorescence radiation at an emission wavelength in response to receiving excitation radiation at an excitation wavelength. The instrument comprises (i) a light source, wherein the light source is configured to emit incident light that includes light at the excitation wavelength of the fluorophore, (ii) a collimator for collimating the incident light from the light source to provide collimated incident light, (iii) a focusing system for directing the collimated incident light onto the surface of the photonic crystal at an angle of incidence and for focusing the collimated incident light to a focal line on the surface of the photonic crystal such that the focal line is substantially parallel to the grating direction and the collimated incident light at the focal line is collimated in a direction substantially perpendicular to the grating direction, and (iv) a detection system configured to detect fluorescence radiation emitted by the fluorophore at an emission angle in response to the collimated incident light directed onto the surface of the photonic crystal.

In some examples, the optical resonance of the photonic crystal has a resonance wavelength at the angle of incidence that corresponds to the excitation wavelength of the fluorophore. In some examples, the optical resonance of the photonic crystal has a resonance wavelength at the emission angle that corresponds to the emission wavelength of the fluorophore. In some examples, the excitation wavelength, angle of incidence, emission wavelength, and emission angle may be such that both the excitation radiation and emission radiation couple to the optical resonance of the photonic crystal.

In some examples, the detection system comprises a CCD camera and a filter, wherein the filter is configured to pass light at the emission wavelength and block light at the excitation wavelength.

In some examples, the focusing system comprises a cylindrical lens and an objective lens. In such examples, the cylindrical lens can have a cylindrical-lens focus at a location in a focal plane of the objective lens, such that the location of the cylindrical-lens focus in the focal plane of the objective lens defines the angle of incidence. The objective lens may also be configured to collect fluorescence radiation emitted from the focal line on the photonic crystal and to direct the collected fluorescence radiation toward the detection system. The focusing system may further include a dichroic mirror that is configured to reflect light at the excitation wavelength and to transmit light at the emission wavelength. For example, the object lens may be configured to direct the collected fluorescence radiation toward the detection system through the dichroic mirror.

In some examples, the fluorophore is coupled to the surface of the photonic crystal at a plurality of discrete locations. In such examples, the instrument may include a movable stage for moving the photonic crystal relative to the objective lens such that each of the discrete locations is exposed to the collimated incident light and the objective lens collects fluorescence radiation emitted from each of the discrete locations and directs the fluorescence radiation collected from each of the discrete locations toward the detection system.

BRIEF DESCRIPTION OF THE DRAWINGS

FIGS. 4A and 4B show example fluorescence images of TNF-α and IL-3 assays on a glass slide acquired using a commercial confocal microarray scanner.

FIGS. 4C and 4D show example fluorescence images of TNF-α and IL-3 assays on a silicon-based photonic crystal acquired using the OCLS instrument of FIG. 3.

FIG. 7A is a cross-sectional schematic view of an example solitary photonic crystal structure.

FIG. 7B is a cross-sectional schematic view of an example cavity-coupled photonic crystal structure.

FIG. 7C an optical image of an example cavity-coupled photonic crystal structure fabricated on a gold-coated silicon wafer.

FIG. 7D is a cross-sectional scanning electron microscope image of an example cavity-coupled photonic crystal structure.

DETAILED DESCRIPTION

1. Overview

Figure 1A:
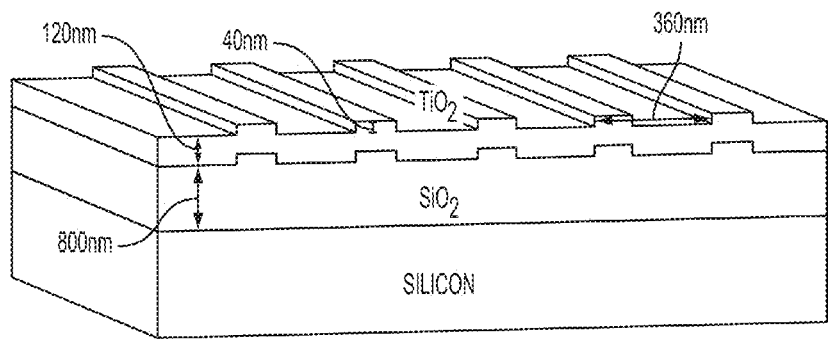
FIG. 1A is a cross-sectional schematic view of an example silicon-based photonic crystal structure that includes silicon, $SiO_2$, and $TiO_2$.

Enhancement of the fluorescent output of surface-based fluorescence assays by performing them upon nanostructured photonic crystal (PC) surfaces can increase signal intensities by >8000×. Using the multiplicative effects of optical resonant coupling to the PC in increase the electric field intensity experienced by fluorescent labels ("enhanced excitation") and the ability of a photonic PC optics ("enhanced extraction"), PC enhanced fluorescence (PCEF) can be adapted to reduce the limits of detection of disease biomarker assays, and to reduce the size and cost of high sensitivity detection instrumentation.

Disclosed herein is a silicon-based PCEF multiplexed biomarker chip. The silicon-based PC structure, comprised of a $SiO_2$ grating that is overcoated with a thin film of high refractive index $TiO_2$, can be produced in a semiconductor foundry for low cost, uniform, and reproducible manufacturing. Further, a silicon-based PCEF chip design can achieve an additional 6× enhancement factor through the incorporation of a Fabry-Perot optical cavity beneath the PC.

Also disclosed herein is a compact detection instrument that efficiently couples fluorescence excitation from a semiconductor laser to the resonant optical modes of the PC, resulting in elevated electric field strength that is highly concentrated within the region <100 nm from the PC surface. The instrument utilizes a cylindrically focused line to scan a microarray in <1 minute. To demonstrate the capabilities of the system, microspot fluorescent sandwich immunoassays using secondary antibodies labeled with Cy5 for two cancer biomarkers (TNFα and IL-3) were performed. Biomarkers were detected at concentrations as low as 0.1 pM. In a fluorescent microarray for detection of a breast cancer miRNA biomarker, the miRNA was detectable at a concentration of 0.6 pM.

A silicon-based photonic crystal (PC) surface can achieve pg/ml-level sensitivity for multiplexed cancer biomarker detection (soluble proteins and miRNA) using photonic crystal enhanced fluorescence (PCEF) to amplify the output of surface-based fluorescent assays. The detection platform includes a PC surface and a detection instrument. The PC surface can be designed to provide optical resonances for efficient coupling to the excitation laser and efficient extraction of fluorescence emission on silicon substrates using $SiO_2$ and $TiO_2$ materials selected to provide negligibly low levels of autofluorescence, thus enabling weak fluorescent signals generated by low concentration analytes to be more easily observed. Furthermore, the Si-based PC allows the sensor to be inexpensively, uniformly, and reproducibly manufactured in a semiconductor foundry. The detection instrument can be designed so that all the light delivered by a miniature solid state laser can be coupled to PC resonant modes by taking advantage of a unique feature of the PC photonic band structure. PC enhancement enables the use of inexpensive components to detect otherwise weak fluorescent signals, resulting in a compact and inexpensive line scanning instrument.

To demonstrate the capabilities of this system, microspot fluorescent immunoassays for two breast cancer biomarkers (TNF-α and IL-3) were performed. Using only 10 µl sample volumes, consistent with detection from a droplet of fluid, the biomarkers were detected at concentrations as low as 0.1 pM. In a fluorescent microarray for detection of a breast cancer miRNA biomarker (miR-21), the miRNA was detectable at a concentration of 0.6 pM. The system can be applied broadly for multiplexed soluble biomarker analysis, particularly for diseases in which no accurate imaging modality exists, where imaging would be cost-prohibitive as an initial screen, or for situations in which noninvasive and frequent biomarker monitoring would be beneficial.

2. Device Surface and Optical Characteristics

The photonic crystal enhanced fluorescence (PCEF) surface includes a nanostructured grating patterned in a thermally grown, low refractive index silicon oxide ($SiO_2$) layer atop a silicon substrate. The grating structure with a fixed period and duty cycle is patterned by deep-UV photolithography, and etched into the silicon oxide layer. Additional details of the PC device dimensions, materials, and fabrication approach are described below. The device fabrication is completed by removal of the photoresist, followed by coating the grating with a high refractive index titanium oxide ($TiO_2$) layer. This periodic arrangement of the high ($TiO_2$) and low ($SiO_2$) index layers results in the characteristic narrow band resonance peak and local electric field enhancement. A cross-sectional schematic view of an example silicon-based photonic crystal structure is presented in FIG. 1A.

Figure 1B:
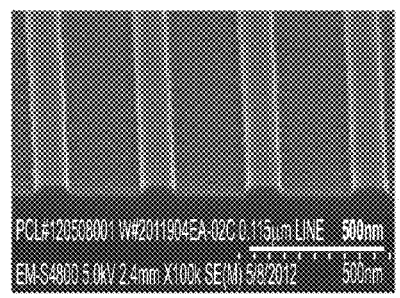
FIG. 1B is a scanning electron micrograph that provides a cross-sectional view of an example grating pattern in the $SiO_2$ layer of a fabricated silicon-based photonic crystal structure before the $SiO_2$ layer is coated with $TiO_2$.
Figure 1C:
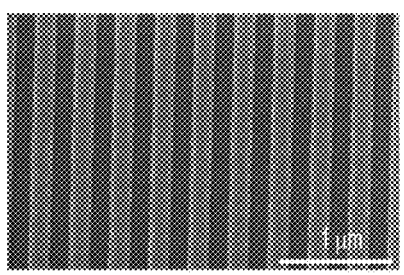
FIG. 1C is a scanning electron micrograph that provides a top view of an example fabricated silicon-based photonic crystal structure after $TiO_2$ coating.
Figure 1D:
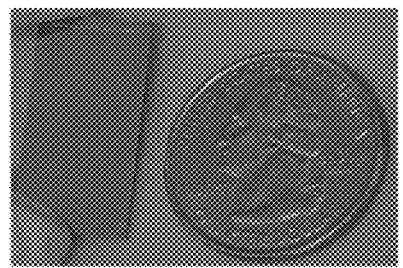
FIG. 1D is a photograph of an example finished silicon-based photonic crystal structure diced into a 1 inch by 0.5 inch piece.

FIG. 1B is a scanning electron micrograph that provides a cross-sectional view of the grating pattern in the $SiO_2$ layer of a fabricated silicon-based photonic crystal structure before the $SiO_2$ layer is coated with $TiO_2$. The grating line width and grating depth were measured to be 131 nm and 37.7 nm, respectively. FIG. 1C is a scanning electron micrograph that provides a top view of the fabricated silicon-based photonic crystal structure after $TiO_2$ coating. The grating period was measured to be 366 nm. FIG. 1D is a photograph of the finished silicon-based photonic crystal structure diced into a 1 inch by 0.5 inch piece.

A commercially available simulation tool for rigorous coupled wave analysis (DIFFRACTMOD, RSoft) was used to aid in the design of a PCEF device that provides electric field enhancement for a TM mode at 632.8 nm. Simulation results suggested the use of a structure with a period of 360 nm, a duty cycle of 36%, a grating depth of 40 nm, and a $TiO_2$ thickness of 120 nm. Prototype devices were fabricated using 8" silicon wafers. A thermal oxide (thickness of 800 nm) was grown on each wafer and a deep UV photolithography process (193 nm, ArF-line) was used to create the grating pattern in the oxide layer. For the lithography step, a 4× binary reticle (6"×6"×0.25 mm, quartz) with a critical dimension tolerance of +/−0.05 μm and uniformity of +/−0.04 μm was used. Precisely timed reactive ion etching steps were then used to transfer the grating pattern from the resist layer into the $SiO_2$ layer. Scanning electron micrographs showing the surface characteristics of these PCs are presented in FIGS. 1B and 1C. The wafer was diced to produce 1"×0.5" chips that were then coated with $TiO_2$ to complete the device (as shown in FIG. 1D).

Silicon-based PCs provide substantial advantages compared to previously reported PCEF surfaces prepared on plastic or quartz substrates. First, these devices can be fabricated on a wafer scale with semiconductor process technology and is thus amenable to inexpensive, high volume manufacturing. Second, the $SiO_2$ and $TiO_2$ materials of the PC have negligibly low levels of autofluorescence, thus enabling weak fluorescent signals generated by low concentration analytes to be more easily observed. Further, silicon-based PCs provide narrow bandwidth optical resonances, which have been shown to generate the greatest fluorescence enhancement factors when the excitation illumination matches the resonance wavelength and coupling angle.

Figure 2A:
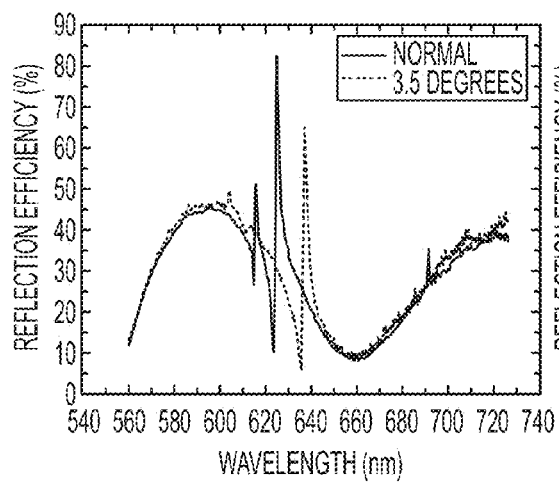
FIG. 2A shows example reflection spectra of a silicon-based photonic crystal illuminated with a broadband light source at normal incidence and at an incidence angle of 3.5 degrees.
Figure 2B:
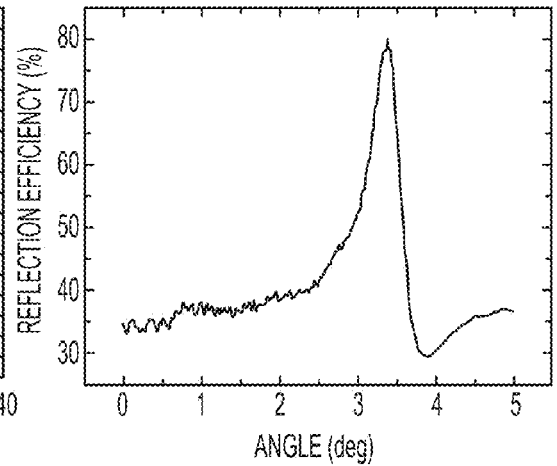
FIG. 2B shows example reflection spectra of a silicon-based photonic crystal illuminated with a collimated solid state laser (at a wavelength of 637 nm) over a range of illumination angles.

The broadband optical properties of the silicon PC (Si-PC) as measured from a finished device are presented in FIG. 2A, which shows reflection spectra for a silicon PC illuminated with a broadband light source at normal incidence and at an incidence angle of 3.5 degrees. The resonant peak at the incidence angle of 3.5 degrees is located at a wavelength of 637 nm, which corresponds to the excitation wavelength of Cyanine-5. The peak has a full width at half maximum (FWHM) of 2 nm. The broad features observed in the reflection spectrum are a result of the thin film interference of the $SiO_2$ and $TiO_2$ thin films, while the high efficiency, narrow reflection peak results from the presence of the PC, and indicates the wavelength at which PC resonance is established. The optical response of a Si-PC over a range of illumination angles and a fixed illumination wavelength of 637 nm from a collimated solid state laser was also obtained (see FIG. 2B), in order to characterize the device angular profile and accurately identify the device resonant angle for a fixed wavelength. The reflection efficiencies shown in FIGS. 2A and 2B are normalized to reflection to a gold mirror.

The success of PCEF is dependent on the ability of the detection instrument to effectively couple light into a PC. The degree of coupling plays a role in the enhancement factor achievable by a PC-instrument combination. The process of characterizing a PC involves the measurement of the wavelength spectra associated with the PC. This is done to ensure suitable positioning of the resonance reflection peak for the PC. The angle spectrum of the PC was then measured at a fixed laser wavelength. The percentage of transmitted light at the resonance condition was indicative of the coupling efficiency of the PC with the instrument. For this purpose, an angle-tuned reflection system can be used for the measurement of the wavelength spectrum. The setup consists of a tungsten halogen lamp (white light), which is coupled to an optical fiber (Ocean Optics Inc.) with a 50 μm core. The output of the fiber is collimated using an achromatic lens. The white light is polarized using a linear polarizer (Thorlabs Inc.) and projected onto the photonic crystal device that is held in a customized holder. The setup design takes advantage of the 1-D PC's relative insensitivity to angle change in the θ-direction. The PC holder is oriented at a fixed angle of θ=5°. The detector is placed at distance of 150 mm from the base of the PC holder and tilted up by 2θ=10°. This orientation allows for the detection of the reflected spectra at normal incidence. The detector height is lower than the height of the illumination beam and is composed of another collimator, which is coupled to a 50 μm core fiber. The other end of the fiber is coupled to a spectrometer (Ocean Optics Inc.). Utilizing commercial software (Spectra suite, Ocean Optics Inc.), the reflected spectrum can be measured. In order to measure the reflected wavelength spectra off normal, the PC holder is mounted on a rotation stage. This stage is then mounted on a 180 mm custom arm that contains the detector mount at the other end. The arm is then sandwiched by another rotation stage. In order to measure the reflected wavelength spectrum at an angle of incidence φ, the top rotation stage is rotated by φ clockwise and the bottom stage is rotated by 2φ counter-clockwise. This allows the detector to collect the reflected wavelength spectra at every angle. Each spectrum is normalized using a gold reflection mirror.

Finite Difference Time Domain (FDTD) computer simulations were used to aid in the design of the structure shown in FIG. 1A, and to thus predict the resonant spectrum expected from the structure. FDTD also enables visualization of the electric field distribution on the PC surface at the resonant coupling condition. Excellent agreement was observed between the simulation and measured broadband optical responses in key parameters such as the spectral location of the peak, the peak width, and its reflection efficiency. The model can be used to estimate the potentially available excitation enhancement provided by a PC structure where the incident excitation light is collimated and matched to the PC resonant coupling condition. In one example, a maximum electric field enhancement of 1767 times the incident electric field and an average electric field enhancement of 401 times and 135 times the incident electric field is achieved for 10 nm and 100 nm tall regions extending above the $TiO_2$ layer into the device superstrate (air, in this case). In general, the goal is to provide a narrow high reflection efficiency peak, as previous work has shown that the potential enhancement is inversely proportional to the bandwidth of the resonance.

3. Objective-Coupled Line Scanning (OCLS) Detection Instrument

One aspect of the Si-PC detection platform is the design of the detection instrument used for fluorescence excitation and imaging of fluorescence emission. The goal of the detection instrument is to illuminate the PC at the wavelength/angle combination that satisfies the resonant condition. Because light focused to a point contains a wide range of incident angles, only a small fraction of the incident light will be resonant with the PC, and thus the enhancement effect provided by point-focused light is not capable of achieving the maximum available enhancement effect. One approach to overcome this problem is to illuminate a broad area of the PC with collimated light, which unfortunately results in substantially reduced excitation intensity compared to a focused beam. Alternatively, one can take advantage of the unique optical properties of the linear PC grating structure, for which the resonant coupling condition only need be satisfied for incident angles oriented perpendicular to the grating lines. A cylindrical lens may be used to provide light that is focused in the plane parallel to the grating, but completely collimated in the plane perpendicular to the grating, thus simultaneously achieving nearly 100% resonant coupling to the PC, and a high intensity focused line of illumination.

Figure 3:
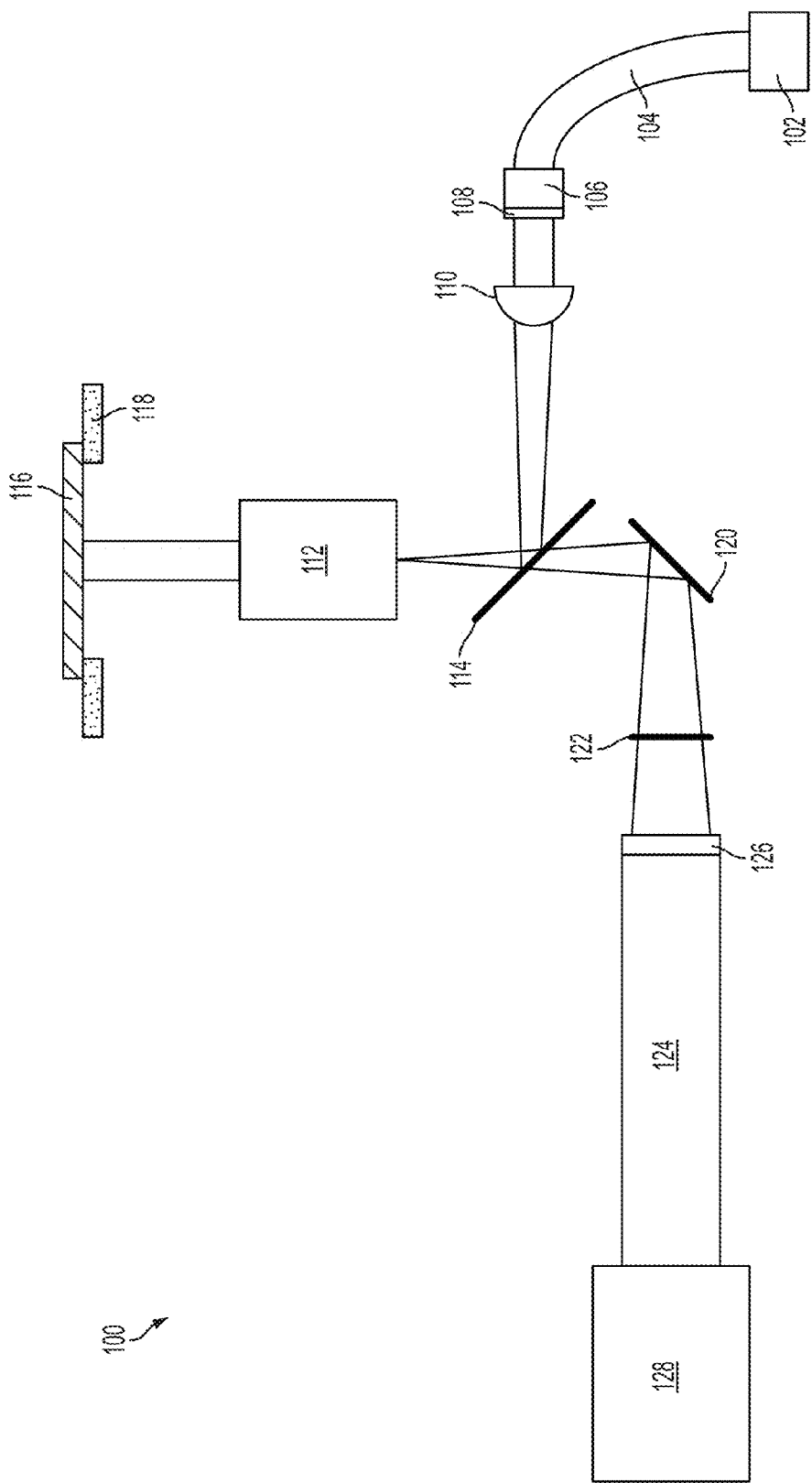
FIG. 3 is a schematic diagram of an example objective-coupled, line scanning (OCLS) instrument that can be used to acquire fluorescence data.

A schematic diagram of an example detection instrument 100 is shown in FIG. 3. A light source 102 is coupled to a polarization maintaining fiber 104, which has a fiber collimator 106 at its tip. The output of the fiber collimator 106 passes through a half-wave plate 108, which can be used to rotate the incident polarization to match the PC-mode of interest, and a cylindrical lens 110. The cylindrical lens 110 focuses the incident light to the back focal plane of an objective lens 112, via a long pass dichroic mirror 114. The objective lens 112 directs the incident light onto a surface of a photonic crystal 116. The photonic crystal 116 may have one or more samples in a microarray on the illuminated surface. The microarray may include a fluorophore that can be excited by the wavelength of the incident light.

By passing the incident light from the laser diode through the cylindrical lens 110 and objective lens 112, the final illumination beam is shaped into an 8 μm×1 mm line that is focused along the direction of the grating in the photonic crystal 116 while remaining collimated in the direction perpendicular to the grating. As shown, photonic crystal 116 is placed on a motorized holding stage 118 that can be translated perpendicular to the illumination beam to scan the area of interest. The cylindrical lens 110, half-wave plate 108, and fiber collimator 106 can be placed as an assembly on a motorized stage (not shown). By tuning the position of this assembly, the incident angle can be modulated in the direction perpendicular to the grating in the photonic crystal 116.

Fluorophore emissions from the fluorophore on the illuminated surface of the photonic crystal 116 are collected by the objective 112, pass through the dichroic mirror 114, are reflected by a turning mirror 120, pass through a bandpass fluorescence filter 122, and enter a lens tube 124 through a projection lens 126, so as to be detected by a CCD camera 128. A fluorescent image of the illuminated surface of the photonic crystal 116 can be obtained by adjustments of the incident angle of the illumination line upon a region of the PC 116 adjacent to the microarray, and then translating the PC holding stage 118 in small increments past the assay region, with the CCD camera 128 gathering a fluorescent intensity image of the line for each motion increment. The fluorescent image of each line can be assembled into a two-dimensional image of fluorescent intensity using software. In a representative example, a single scan can be performed in less than 1 minute.

In one example, light source 102 is a solid-state laser (AlGaAs, 70 mW) that emits light at a wavelength of 637 nm (an excitation wavelength of Cyanine-5), the objective lens 112 is a 10× microscope objective (Olympus Plan N) of focal length 18 mm. Further, in this example, the solid-state laser is coupled to the polarization maintaining fiber 104, and the fiber tip is coupled to the fiber collimator 106 giving a highly collimated output beam 3.4 mm in diameter. The output of the fiber collimator 106 is then passed through the half-wave plate 108, which is used to rotate the polarization of the output beam to match with the PC-mode of the PC 116 to be excited. The cylindrical lens 110 (having a focal length of 100 mm in this example) focuses the light to a line onto the back focal plane of the objective 112 via the dichroic mirror 114. The output of the objective 112 is thus a laser beam focused to a line onto PC 116. The motorized sample stage 118 (in this example, model MS-2000 from Applied Scientific Instrumentation, Eugene, Oreg.) is translated perpendicular to the laser line for a fast scan (750 lines/second). The fluorescence image is constructed by sequential scanning across the PC 116 in fixed increments. The PC 116, placed at the focal plane of the infinity-corrected objective 112, interacts with a beam that is collimated in one plane but focused in the orthogonal plane.

In this example, the assembly of the cylindrical lens 110, half-wave plate 108, and fiber collimator 106 are mounted on a two-dimensional motion stage (not shown). The stage is manually adjustable in one plane and automated in the other. The manual adjustment is utilized to fine-tune the focus of the beam onto the back focal plane of the objective lens 112. In order to tune the angle of incidence onto PC 116, the line-focused beam is translated on the back focal plane of the objective 112, by tuning the position of the cylindrical lens-wave plate fiber collimator assembly. This fine stepping is achieved by utilizing a motorized linear stepping stage (Zaber LSM-25). The result is a change in the incident angle.

The angle of incidence may be adjusted so that the incident light, which has a wavelength that corresponds to an excitation wavelength of the fluorophore (e.g., 637 nm for Cyanine-5) on the photonic crystal 116, also satisfies a resonance condition of the photonic crystal 116. By using incident light to excite the fluorophore that has a combination of wavelength and angle of incidence that corresponds to an optical resonance of the photonic crystal, fluorescence enhancement can be achieved.

The emitted fluorescence signal is collected by the objective 112 and projected onto CCD camera 128 (in this example, model 9100C from Hamamatsu) through lens tube 124 by projection lens 126 (having a focal length of 150 mm in this example). The bandpass fluorescence filter 122 inserted between the objective 112 and the projection lens 126 passes the fluorescence signal but blocks the excitation laser beam. If the wavelength and angle of the collected fluorescence signal matches a resonance condition of the photonic crystal 116, then fluorescence enhancement can be achieved.

As noted above, fluorescence enhancement can be achieved by selecting a combination of wavelength and angle that matches a resonance condition in the photonic crystal for either the incident light used to excite the fluorophore or the fluorescence light emitted by the fluorophore. In some instances, an even greater amount of fluorescence enhancement can be achieved by having both the incident light used to excite the fluorophore and the fluorescence light emitted by the fluorophore correspond to an optical resonance of the photonic crystal. In one example, Cyanine-5 is coupled to a surface of a silicon-based photonic crystal in which the resonance wavelength varies as a function of angle such that the resonance wavelength at 0° (normal incidence) corresponds to the excitation wavelength of the fluorophore (637 nm) and the resonance wavelength at about 7° corresponds to the emission wavelength of the fluorophore (670 nm). Thus, with the proper selection of the photonic crystal, the fluorophore, and the angles used for excitation and emission, both the excitation radiation and the emission radiation can couple to the optical resonance of the photonic crystal.

The image acquisition process can be automated, for example, using a C# based user interface. The software can provide a synchronous integration of the various components of the instrument. In one approach, drivers for the Hamamatsu CCD, Zaber linear stepping motor and the ASI XYZ-sample stage are written individually and then synchronized using a single program. The final software can be used to capture the angle spectrum of a PC as well as perform fluorescence measurements.

In one example, the user interface allows for inputs of start and stop positions for defining a XY scan range and an angle scan range. The step size for the XY scan range can be 2 µm, corresponding to the effective width of an individual pixel on the CCD. This step size can also provide oversampling. For example, given a beam width of 6 µm and a 2 µm step size, the images are oversampled by a factor of 3 in the scan direction. The oversampling can be done so that only the peak intensity at each pixel is used to generate the image. If a step size equal to the focus beam width were used, one would encounter a variability of ±25% in the scan direction as opposed to a variability ±6%. The tradeoff here is a 3× slower scan speed due to the shorter step size. Further, if the fluorescence emitted for all three frames is aggregated, the final intensity value for that pixel should be over 2× without increasing the laser power or integration time. Thus, a processing algorithm can artificially enhance the integration time as well. This processing algorithm can lower the variability in the scan direction by 3×, due to the flat-top effect for a Gaussian profile. Theoretically, a Gaussian convolved with a Gaussian gives a flattop beam. This algorithm results in an optical convolution that allows reduction of variability and hence noise.

4. Fluorescence Enhancement Characterization

Initial bulk fluorescence enhancement measurements on the Si-PC as compared to an unpatterned glass control substrate were performed by spin coating an LD-800 (dye) doped layer of SU-8 (photoresist) onto cleaned devices. Fluorescence data on all substrates was acquired using the OCLS instrument at a fixed laser power of 3 mW. CCD exposure time was adjusted to maximize fluorescence output on each substrate and gathered measurements were later normalized based on the exposure setting to allow for comparisons between substrates. Fluorescence signal enhancement is defined as the ratio of the system dark noise subtracted maximal fluorescence intensity of the PC to a control glass substrate. When scanned on resonance, a 96.7× factor in fluorescence enhancement was observed on the Si-PC as compared to its off resonance condition, representing the gain supplied by the enhanced excitation effect.

Next, we characterized the device fluorescence enhancement performance in the context of a simple microarray assay where microspots of streptavidin labeled with Cyanine-5 were deposited on a silane functionalized PC. Such an experiment provides a measure of net fluorescence signal intensity enhancement as well as another important parameter of signal-to-noise ratio (SNR) enhancement. Enhancements in the SNR are especially meaningful as they more readily translate to lowering the limits of detection for a biological specimen because such gains indicate an enhancement in the fluorescence intensity that is greater than any associated increases in the background fluorescence intensity. An average fluorescence signal enhancement of 113.5× and an average SNR enhancement of 10.3× was observed when the Si-PC resonance was excited.

5. Fluorescence Immunoassay and miRNA Microarray

The performance of the Si-PC coupled with the OCLS detection system was next studied in the context of a microspot-based fluorescent sandwich immunoassay. Si-PCs paired with glass control slides were each partitioned into eight sectors. The eight sectors included four replicate microspots of capture antibodies for IL-3 and four replicate microspots of capture antibodies for TNF-α, which were printed using a dip-pen nanolithography system. A mix of IL-3 and TNF-α was assayed in these sectors over a range of 7 concentrations in a 3-fold dilution series with a starting concentration of 16.6 ng/mL for IL-3 and 2 ng/mL for TNF-α. Additional assay details are described below. Fluorescence images for the Si-PC were obtained with the OCLS, and fluorescence images for the glass control slide were obtained using a commercially available confocal microarray scanner (Tecan-LS, laser wavelength of 632.8 nm). FIGS. 4A and 4B show representative fluorescence images of the microspots on the glass control slide. FIGS. 4C and 4D show representative fluorescence images of the microspots on the silicon-based photonic crystal at different assayed concentrations. The assayed concentrations for TNF-α were 222.22 pg/ml in FIG. 4A, 24.60 pg/ml in FIGS. 4B and 4C, and 2.74 pg/ml in FIG. 4D. The assayed concentrations for IL-3 were 1.85 ng/ml in FIG. 4A, 205.76 pg/ml in FIGS. 4B and 4C, and 22.86 pg/ml in 4D.

Figure 5A:
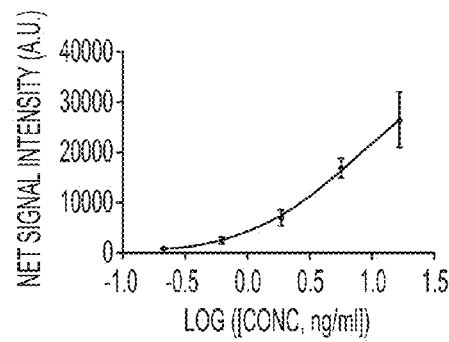
FIG. 5A is an example dose-response curve obtained for IL-3 on a glass slide.
Figure 5B:
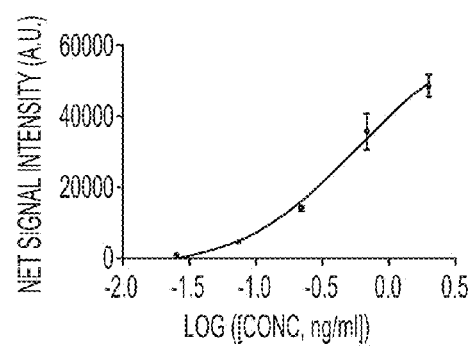
FIG. 5B is an example dose-response curve obtained for TNF-α on a glass slide.
Figure 5C:
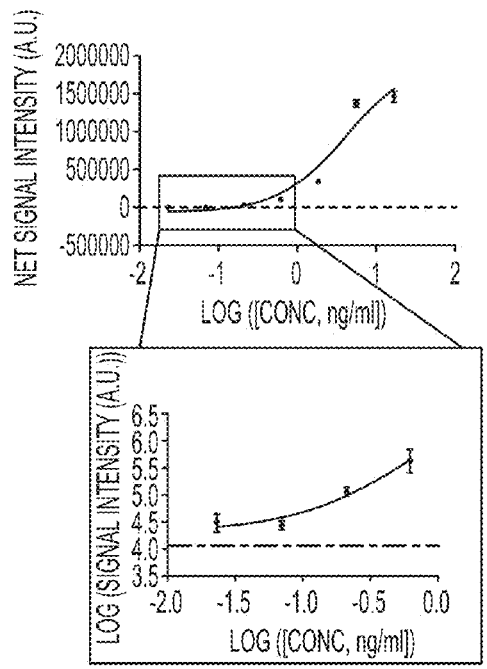
FIG. 5C is an example dose-response curve obtained for IL-3 on a silicon-based photonic crystal.
Figure 5D:
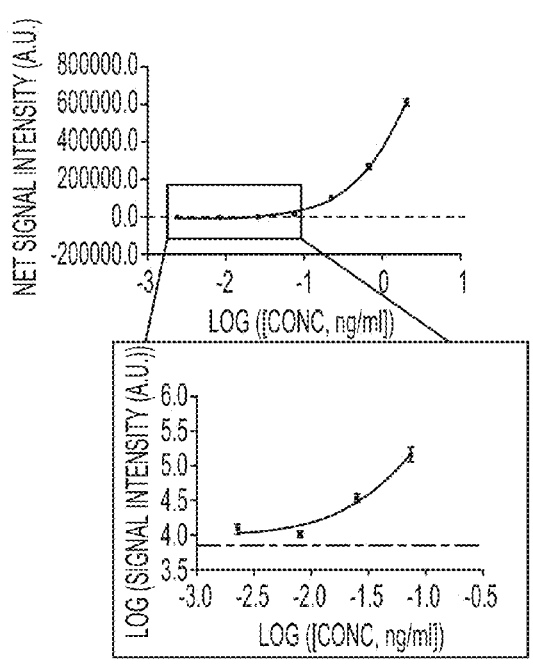
FIG. 5D is an example dose-response curve obtained for TNF-α on a silicon-based photonic crystal.

The dose-dependent response of each antigen assayed is presented in FIGS. 5A-5D, including dose-response curves obtained on the glass slide for IL-3 (FIG. 5A) and TNF-α (FIG. 5B), and dose-response curves obtained on the silicon-based photonic crystal for IL-3 (FIG. 5C) and TNF-α (FIG. 5D). The data shown are mean values of four replicate spots. The five highest concentrations out of a total of seven assayed concentrations were detectable on the glass side. The lowest concentrations of TNF-α and IL-3 detected on the glass surface were 24.69 pg/mL and 205.76 pg/mL, respectively. In comparison, all seven assayed concentrations were detectable on the PC with the lowest concentrations being 2.74 pg/mL and 22.86 pg/mL for TNF-α and IL-3 with replicate averaged SNRs of 24.6 and 45.4, respectively. The horizontal line shown in the enlarged portions of FIGS. 5C and 5D represents the fluorescent intensity value measured in the regions directly adjacent to the microarray spots, thus establishing the local fluorescent background level. Negative controls performed by exposure of capture antibodies to a buffer-only sample resulted in no observable fluorescence signal above this background.

Figure 6:
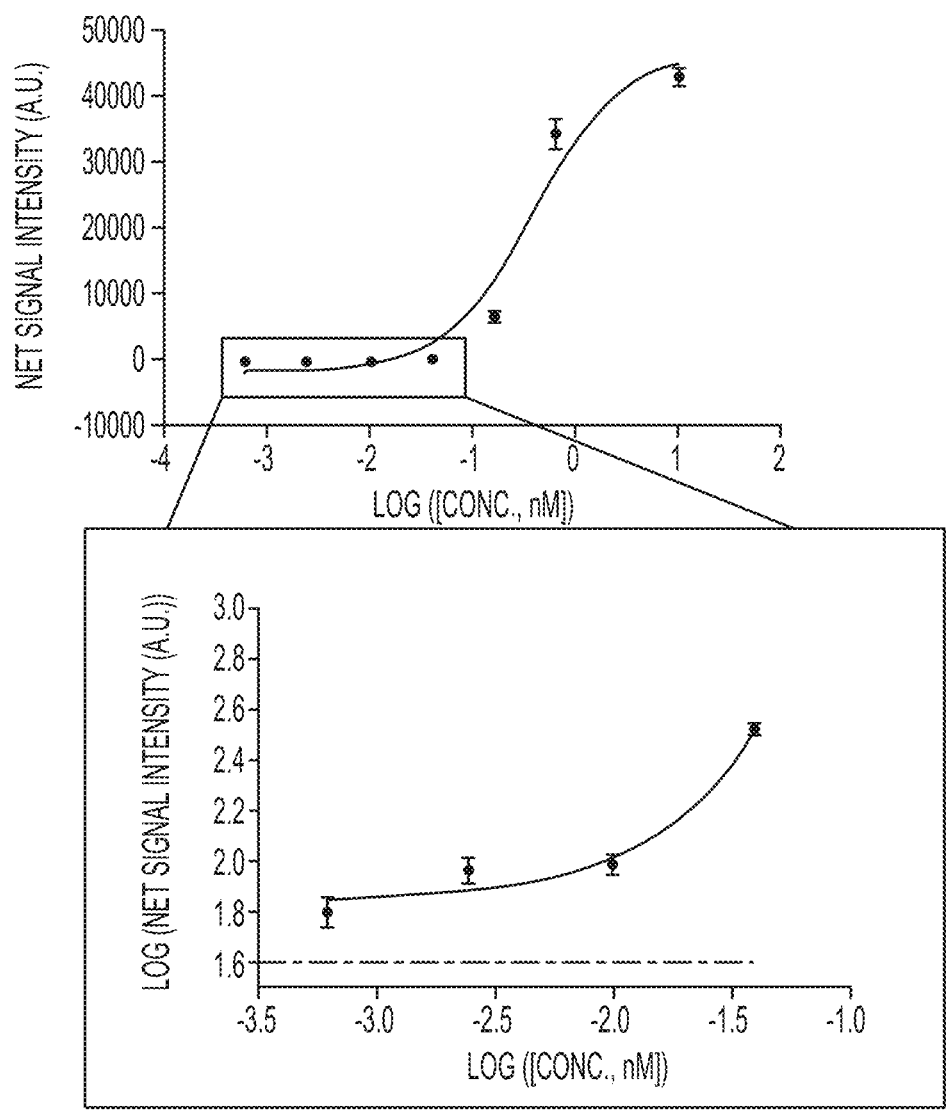
FIG. 6 shows an example dose-response curve for miR-21 assayed on a silicon-based photonic crystal over a concentration range of 10 nM to 0.6 pM.

Finally, we characterized the performance of a miRNA microspot assay on the Si-PC where we chose to assay miR-21, a miRNA sequence implicated in the progression of breast cancer. The miR-21 target miRNA sequence was assayed on the PC at the following seven concentrations: 10 nM, 2.5 nM, 156 pM, 39 pM, 9.8 pM, 2.4 pM, and 0.6 pM. All seven concentrations yielded detectable signals with the lowest concentration of 0.6 pM having a replicate averaged spot SNR of 3.8. The dose response of the assayed set of concentrations is presented in FIG. 6. The data shown are mean values of sixteen replicate spots. The horizontal line in the enlarged portion represents the local fluorescent background level.

Spot segmentation and intensity calculations of the constructed fluorescence images were performed using either ImageJ or Genepix Pro 6.1 (Molecular Devices). Net spot intensity was calculated as the local background subtracted spot intensity where the local background is an annular region around a given spot. Spot SNR was calculated as the local background subtracted spot intensity divided by the standard deviation of the local background.

6. Methods a. LD-700 Assay for Fluorescence Polarization Enhancement Characterization To characterize the fluorescence enhancement afforded by the silicon PCs, a fluorescent dye, LD-700 (Exciton, Inc., Dayton Ohio; excitation peak=647 nm, emission peak=673 nm) was used. The dye was mixed with SU-8 which served as the carrier and this solution was spun coated onto the device. SU-8 2000.5 was mixed with an SU-8 thinner (Microchem Corporation) at a ratio of 1:20 (by volume). The stock LD-700 dye solution was diluted in methanol to a concentration of 100 nM (53.8 ng/mL). The LD-700 was then mixed with the thinned SU-8 solution in 1:1 ratio (by volume) and the resulting solution was spun coated on the silicon PC and control glass substrates (Spincoater P6700, 5000 rpm, 30 seconds).

b. Device Surface Functionalization

The PC devices were functionalized using a vapor-phase epoxysilane process. The epoxysilane chemistry was chosen for its low background fluorescence and high binding capacity to capture antibodies. The devices were first cleaned by sonication in 2" petri dishes of acetone, isopropanol, and deionozied (DI) water for 2 minutes each. The devices were then dried in a stream of $N_2$ and then treated in an oxygen plasma system (Diener, Pico) for 10 minutes (power of 100 W, pressure of 0.75 mTorr). The backside of each device was then adhered to the inside of a screw top lid of a 2" glass container. At the base of the container, 100 uL of (3-Glycidoxypropyl) trimethoxysilane (GPTS, Sigma Aldrich, Saint Louis, Mo.) was placed and the screw top lid was securely placed over the dish. After securely tightening the lids, each dish with a device adhered to its lid was placed in a vacuum oven for an overnight incubation at a temperature of 80° C. and a pressure of 30 Torr. The devices were then detached from the lids and sonicated in 2" petri dishes of toluene, methanol, and DI water for 2 minutes each and dried under a stream of $N_2$. Standard glass microscope slides that served as controls were also silanized using the same protocol but with appropriately sized glassware.

c. SA-Cy5 Microspot Assay for Fluorescence Enhancement Characterization

To evaluate fluorescence enhancement, cyanine-5 (Cy5) conjugated streptavidin (GE Healthcare) at a concentration of 100 µg/mL in phosphate buffered saline (PBS) with 60% v/v glycerol was printed onto the substrates for a total of 14 replicate spots with a diameter of 45±6 µm. Protein spots were printed using an electrohydrodynamic jetting (e-jet) system previously introduced here as a non-contact method for high resolution printing. The print head consists of a syringe acting as an ink reservoir that is then connected to an Au—Pt coated (thickness of ~10 nm), glass, luer-tipped micropipette nozzle (World Precision Instruments) with an inner diameter of 5 µm. Through a combination of capillary force and an appropriately selected back pressure that is applied to the fluid, a spherical meniscus is formed at the tip of the nozzle. A voltage is then applied between the nozzle tip and substrate to draw the meniscus into a cone and jetting from this cone creates printed features on the substrate. By modulating the back pressure, the separation distance between the nozzle and substrates, and the applied voltage, one can modulate the jetting frequency and droplet size. A pulsed-voltage mode with a square-wave function was used to create lines of droplets to form arrays.

After printing, the substrates were incubated overnight in a humid chamber and then rinsed three times in a 0.05% Tween solution of PBS, followed by a final set of three rinses in ultrapure deionizied water. The substrates were then dried under a stream of nitrogen and the fluorescence data was acquired soon thereafter.

d. Fluorescent Sandwich Immunoassay

The protein microarrays were produced using a desktop nanofabrication system, NLP2000, based on DPN technology (NanoInk Inc., Skokie, Ill., USA). Prior to printing, the tips, DPN Probes type M-ED Side M-2 with 12 A frame cantilevers (NanoInk Inc., Skokie, Ill., USA), with a pitch between each pen of 66 µm, were plasma cleaned for 40 second at low RF-value, using a gas mixture of Oxygen/Argon (21%/79%) at 200 mTorr using a Plasma Cleaner (PDC-32G) (Harrick Plasma, Ithaca, N.Y., USA). Two type of cytokines interleukin 3 (IL-3) and tumor necrosis factor (TNF-α) (R&D Systems Inc., Minneapolis, Minn.) capture antibodies were printed on epoxysilane modified PC slides and Nexterion 1"×3" Slide E (Schott A G, Maintz, Germany) control glass microscope slides. The printing was performed under a controlled environment using an environmental chamber (ambient temperature and 30% relative humidity). The antibodies (~5.0 mg/mL) where diluted in proprietary printing buffer (NanoInk Inc., Skokie, Ill., USA); the printing buffer is formulated to keep the protein moisturized and to preserve their active and folded states. Four pens out of 12 pens were used to print two cytokine, a positive control (goat-anti Rabbit IgG) at 2.0 mg/mL and a negative control (Normal Rabbit IgG labeled with Alexa-Fluor-555) at 3.2 mg/mL. Each PC holds 10 subarrays and the glass slides hold 48 subarrays in a 4×12 format. Each subarray contains 4 sets of 4 replicate spots per antibody for a total of 16 spots. Spot diameters were measured to be 15±3.7 µm. The printed substrates were incubated in a sealed box with a desiccant for two days at 4° C. Next, the slides were placed in a 48 well format slide module assembly (NanoInk Inc., Skokie, Ill., USA), where each well could hold up to 12 pt. The arrays were blocked with casein blocking buffer (BioRad, Hercules, Calif.) for 1 h. All incubations were performed at room temperature. The arrays were then washed three times with 0.01% (v/v) tween 20 in PBS (PBST) and then each well was incubated with a 10 µL mixture of different antigens concentration in casein buffer for three hours. This was followed by three rinses in PBST after which the glass slides was incubated in a bulk dish with 2 ml mixture of 1 µg/mL biotinylated detection antibodies while the PC substrates were incubated with only 10 µL of the biotinylated detection antibody mixture in each well of the slide module assembly for 1 hour. The PC substrates and glass slides were then washed three times with PBST, followed by the incubation with a 1 µg/mL solution of Alexa-Fluor-647 conjugated streptavidin (Invitrogen) for 30 minutes. Finally, the devices were washed 5 times with PBST and followed by a quick dip in DI water (3 second) to remove the salt, spin dried and then scanned. Antigen standard curves were generated by using a 3-fold dilution scheme for a total of 7 concentrations. The starting concentrations for IL-3 and TNF-α were 16.6 ng/mL and 2 ng/mL, respectively.

e. Fluorescent miRNA Detection

In this experiment the miR-21 probe-target sequence was assayed in a microspot format. The capture oligonucleotide sequence (5'-TCA-ACA-TCA-GTC-TGA-TAA-GCT-A-3', purchased from IDT DNA Technologies, Coralville, Iowa) was modified to have a 6-carbon chain amine modification at the 5' end. This probe sequence was printed at a concentration of 50 µM in a printing buffer of autoclaved, Milli-Q water (resistivity of 18.2 MΩ·cm$^{-1}$) with 80% v/v of glycerol (Sigma-aldrich, Saint Louis, Mo.). A polydimethylsiloxane-based (PDMS; Sylguard 184, Dow Corning, Midland, Mich.) 8-well mold was used to create isolated, 4 mm diameter wells on the printed substrates. The mold was prepared from a ~1 mm thick film of cured PDMS, rinsed with IPA and DI water, dried under $N_2$ and firmly placed over the substrate. Through Van-der-Waal's forces, the mold remained adhered to the substrate for the course of the experiment.

In each well, two rows of 8 spots were created for a total of 16 replicate spots per well. Printing was performed in ambient temperature and humidity conditions using the e-jet tool. Upon printing, the substrates were placed in a petri dish with a moist kimwipe at its base to keep the petri dish humid. The dish was sealed with parafilm and incubated overnight. The substrates were then rinsed in a wash buffer of DI water with 0.2% v/v of sodium dodecyl sulfate (SDS; purchas Sigma Aldrich, Saint Louis, Mo.), followed by two additional rinses in DI water, and then dried under a stream of $N_2$. The target miRNA sequence (5'-UAG-CUU-AUC-AGA-CUG-AUG-UUG-A-3'; IDT DNA Technologies, Coralville, Iowa) was labeled with Cyanine-5 at the 5' end. Dilutions of the target sequence was prepared in a buffer of 5× saline sodium citrate buffer (SSC, containing 75 mM sodium citrate and 750 mM sodium chloride) containing 10% v/v of formamide and 0.1% v/v of SDS (all reagents were molecular biology grade and were purchased from Sigma Aldrich, Saint Louis, Mo.). Seven concentrations of the target miRNA sequence were assayed over a concentration range of 10 nM-0.6 pM; data was obtained from six replicate spots per concentration. For the hybridization step, the substrate was placed in a sealable, rubber chamber and 10 µL of each miRNA dilution was added to a unique well on the substrate. The chamber was sealed and left overnight in a water bath at a temperature of 42° C. After the incubation period, all wells were aspirated, the PDMS mold was detached, and the substrates were rinsed in the following three buffers: 1×SSC containing 0.2% v/v of SDS, 0.2×SSC containing 0.2% v/v of SDS, and finally 0.1×SSC. The substrates were dried under a stream of $N_2$ and imaged immediately thereafter.

7. Optical Cavity for Additional Enhancement

Coupling of multiple resonators can lead to interesting optical properties like increase in Q, changes in electric fields, or modification of the far-field reflection properties, that can improve detection in sensing applications. Disclosed herein is a coupled-cavity photonic crystal structure. The structure operates by coupling one-dimensional (1D) PC modes to the modes of an underlying Fabry-Perot type optical cavity. This coupling of the two modes results in even higher evanescent fields on the surface of the PC when compared to the fields when the light is resonantly coupled to a PC without an underlying cavity coupled to it. The experimental results are also supported by a quantitative theoretical investigation of the cavity-coupled PC structure using rigorous coupled wave analysis (RCWA) electromagnetic modeling.

The structure of a solitary photonic crystal structure (FIG. 7A) is shows in comparison to a cavity-coupled photonic crystal structure (FIG. 7B). Adding a layer of gold under the PC at a specific distance forms the cavity-coupled PC structure. The solitary PC structure is comprised of a periodic linear grating structure (Λ=360 nm, depth, d=60 nm) that is patterned in SU8 resist by solvent-assisted soft imprint lithography. A blanket deposition of a $TiO_2$ film (thickness, t=120 nm) is applied by sputtering on top of the imprinted structure. Previous work has shown that an optimal design for PC enhanced fluorescence utilizes transverse magnetic (TM) polarized light (polarization perpendicular to grating direction) for normal excitation and transverse-electric (TE) polarized light (polarization parallel to grating direction) for extraction of the emitted fluorescence signal. Therefore, the PC resonance was designed to be at normal-incidence excitation (θ=0°) for TM polarized light from a λ=632.8 nm, He—Ne laser for fluorescence excitation. The geometry of the structure and the indices of the surrounding dielectric media determine the resonance wavelength of the PC. The optical cavity strongly modifies these PC resonances. Here a 1D-PC, formed by a linear grating structure in low refractive index (RI) polymer with high RI $TiO_2$ on top, optically couples constructively or destructively to the modes of the underlying optical cavity formed between the PC and the gold layer that acts as a mirror underneath the PC. FIG. 7C shows a large area optical image of the cavity-coupled PC fabricated on a 2 inch gold-coated silicon wafer. FIG. 7D shows a cross-sectional scanning electron microscope (SEM) image of the fabricated cavity-coupled photonic crystal structure, showing a layer of gold on a silicon substrate, a SU8 cavity, a one-dimensional grating in the SU8, and a coating of $TiO_2$ on the grating.

Figures 8A, 8B:
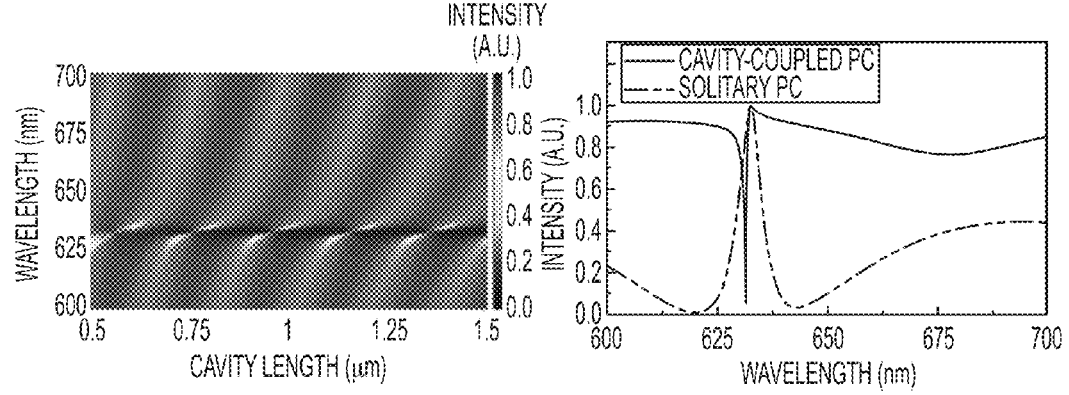
FIG. 8A shows rigorous coupled wave analysis (RCWA) simulated data for far-field reflection of an example cavity-coupled photonic crystal for various cavity lengths.
FIG. 8B shows RCWA simulated data for far-field reflection as a function of wavelength for an example cavity-coupled photonic crystal and a solitary photonic crystal.

RCWA simulations (RSOFT Inc.) were performed to model the coupling between the optical cavity and the PC. The results are shown in FIG. 8A-8D. FIG. 8A shows far-field reflection spectra computed by RCWA for a cavity-coupled PC for different lengths of the cavity and the incidence angle of θ=0° that corresponds to the resonance coupling angle of the PC. The coupling region is represented as the regions in the plot where the reflection from the device becomes a minimum. This occurs when the incident photon resonates within the cavity before it is either scattered or absorbed by the structure.

As shown in FIG. 8A, the coupled mode repeats itself for about every 220 nm of added cavity length. This length corresponds to ~$\lambda_{eff}/2$ that satisfies the condition for constructive interference within the cavity. Here $\lambda_{eff}=\lambda/n_{eff}$ is the effective PC resonance wavelength in the cavity. Thus, the PC resonances repeat with the changes in the cavity length as they come into and out of overlap with the cavity modes.

Figures 8C, 8D:
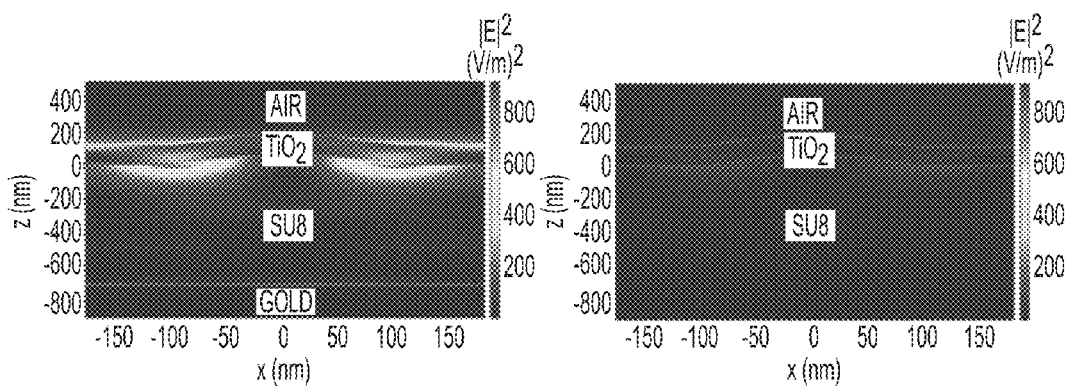
FIG. 8C shows RCWA simulated data of a near-field electric field distribution for an example cavity-coupled photonic crystal.
FIG. 8D shows RCWA simulated data of a near-field electric field distribution for an example solitary photonic crystal.

FIG. 8B shows far-field reflection spectra for a cavity-coupled photonic crystal with a cavity length of 740 nm, in comparison to that of a solitary photonic crystal. With the resonant photon now trapped inside the cavity resulting in a strong sharp dip in the reflection, the cavity not only inverts the reflection response of the device but also enhances the resonance as seen by the increase in the evanescent electric fields on the surface of the photonic crystal, as shown in FIG. 8C (cavity-coupled photonic crystal) and FIG. 8D (solitary photonic crystal).

The subwavelength grating was fabricated by solvent-assisted soft imprint lithography. A soft stamp with a negative surface structure of the finished grating was used for imprinting. The stamp was prepared by spin coating Hard-PDMS (a mixture of poly(7-8% vinylmethylsiloxane)-(dimethylsiloxane), 1,3,5,7-tetravinyl-1,3,5,7-tetramethylcyclotetrasiloxane, Xylene and poly(25-30% methylhydrosiloxane)-(dimethylsiloxane)) onto an 8-inch diameter silicon "master" wafer that had been previously prepared with a positive surface structure of the finished device grating by deep UV lithography. After spin-coating the Hard-PDMS on the silicon wafer, a thick layer of Soft-PDMS (10:1 Sylgard 184) was poured over it to provide mechanical strength for handling the stamp. The master wafer with both layers of PDMS on top of it was heat cured overnight in an oven at 65° C. After curing, the stamp was peeled away from the master wafer and cut into smaller squares. The cavity-coupled PC and the solitary PC were fabricated on a 2-inch diameter Si wafer. SU8 2000.5 was chosen as the polymer that forms the low refractive index layer for the PC and also the cavity layer for the cavity-coupled PC. The solvent assisted imprinting process is performed by first spin coating SU8 onto a clean substrate. A 200 nm gold-coated Si wafer served as the substrate for cavity-coupled PC while a bare Si wafer was the substrate for solitary PC. For the case of the solitary PC, ~1 um thick SU8 was applied by spin coating in two layers. This ensures that Si reflectivity has no effect on the resonance modes of the PC and the modes are only determined by the refractive index of SU8 (n=1.46), the refractive index of $TiO_2$ (n=2.43) and the dimensions of the grating. For the cavity-coupled PC, a SU8 thickness of ~750 nm was spin-coated onto the wafer. After spin coating, SU8 was prebaked at 75° C. for 2 min. A small amount of ethanol was then used to wet the SU8 surface before pressing the substrate against the stamp. The stamp was pressed upon the SU8 coated wafer until the ethanol evaporated (~45 min.), after which the stamp was peeled away and the wafer was UV cured for 2 min. and then hard baked at 90° C. for 2 min. Finally, $TiO_2$ (thickness, t=120 nm) was sputtered onto the grating.

Figure 9A:
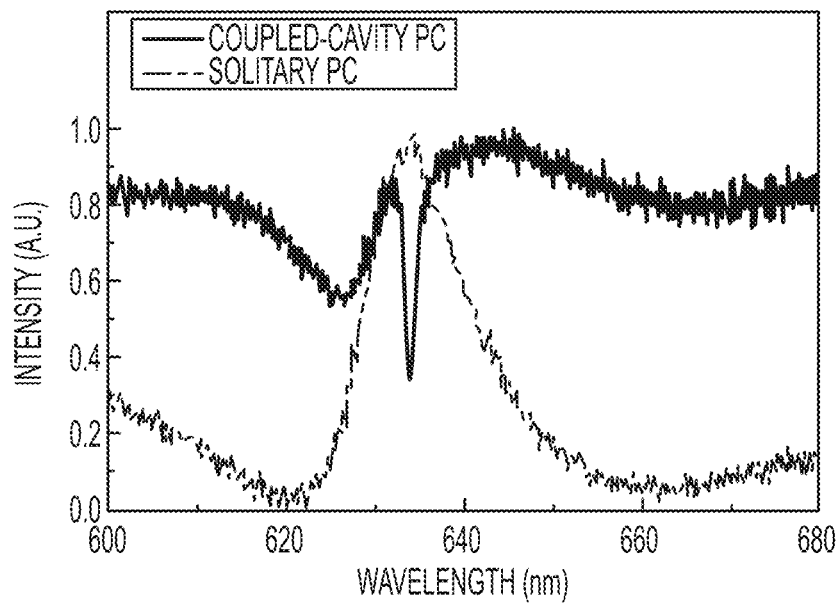
FIG. 9A shows experimental far-field reflection data as a function of wavelength for an example cavity-coupled photonic crystal and for an example solitary photonic crystal.

FIG. 9A plots the measured far-field reflection for the cavity-coupled PC for the cavity length of 750 nm and the solitary PC with the incidence angle of the white light at 0=0°. The reflection spectra were collected by a fiber-coupled collimating lens with its distal end connected to a spectrometer with a wavelength resolution of 0.06 nm (Ocean Optics HR 4000). The measured spectra indicates that the presence of the cavity beneath the PC results in an inversion of the resonance characteristic from a reflective maxima to a reflective minima, as predicted by the RCWA model.

Figure 9B:
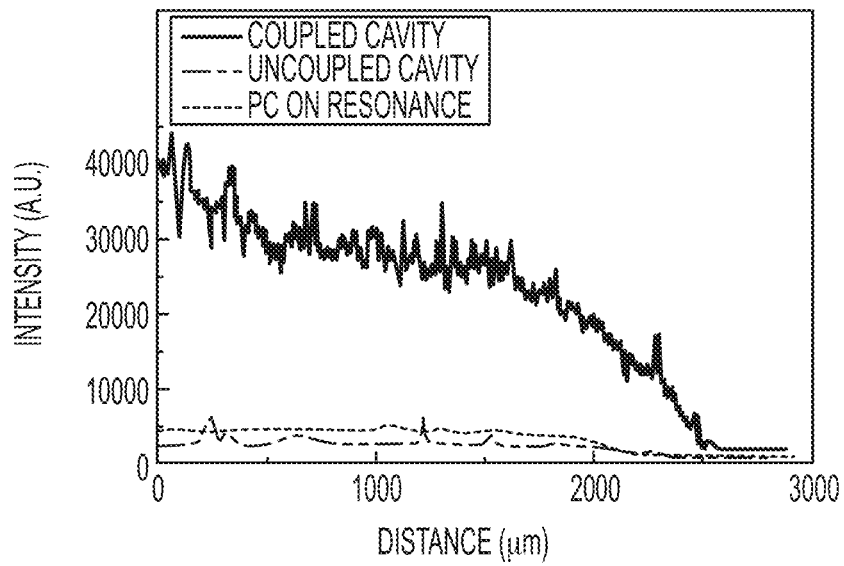
FIG. 9B show intensity profiles for PPL-Alexa 647 dye on an example cavity-coupled photonic crystal, an example photonic crystal with an uncoupled cavity, and for an example solitary photonic crystal.

In order to demonstrate the enhancement in the SNR detection of surface attached fluorophores on the cavity-coupled PC surface, a detection experiment using a dye-labeled protein was performed. Dye-labeled polypeptide, Alexa 647-Poly-Phe-Lysine (PPL-Alexa 647) was applied using a pipette at a concentration of 30 μM on three devices: a cavity-coupled PC with resonance cavity length of 750 nm, a cavity-coupled PC with a non-resonant cavity length of 650 nm, and the solitary PC surface. After overnight incubation, the devices were washed by gently dipping them in deionized water for 60 sec. Each spot of fluorophore-tagged protein has a diameter of approximately 4 mm. Fluorescent images of the labeled protein spots were obtained using a commercially available confocal laser scanner (Tecan, LS-Reloaded) equipped with a TM polarized λ=632.8 nm He—Ne laser. The angle of incidence of the laser can be tuned from θ=0° to θ=25° and using a numerical aperture of 0.04 to focus the light, only a portion of the illumination is applied at the resonant coupling condition. The measured images were analyzed by image processing software (ImageJ). FIG. 9B plots the intensity cross section through the dye-labeled protein spot on each device structure. The angle of incidence for the laser was θ=0° to correspond with the resonance coupling angle of the PC. The fluorescence intensity on the cavity-coupled PC is higher than both the solitary PC and the PC with underlying off-resonance cavity length, showing that the increase in the evanescent fields due to the coupling of the two modes gives rise to the enhancement. From the intensity plot, the increase in the signal to noise ratio for the dye labeled polypeptide on the cavity-coupled PC was calculated as 6× when compared to the solitary PC, and 10× when compared to the off-resonant cavity PC. The noise here is defined as the standard deviation in the background intensity around the spot.

8. Conclusion

Silicon-based PCs provide substantial advantages compared to previously reported PCEF surfaces prepared on plastic or quartz substrates. First, these devices can be fabricated on a wafer scale with semiconductor process technology and is thus amenable to inexpensive, high volume manufacturing. Second, the $SiO_2$ and $TiO_2$ materials of the PC have negligibly low levels of autofluorescence, thus enabling weak fluorescent signals generated by low concentration analytes to be more easily observed. As demonstrated, silicon-based PCs provide narrow bandwidth optical resonances, which have been shown to generate the greatest fluorescence enhancement factors when the excitation illumination matches the resonance wavelength and coupling angle.

What is claimed is:

1. A photonic crystal structure, comprising:
    a silicon substrate;
    a first dielectric having a first index of refraction, wherein the first dielectric has a first surface facing the silicon substrate and a second surface opposite the first surface, wherein the second surface has a grating structure formed therein;
    a second dielectric having a second index of refraction that is higher than the first index of refraction, wherein the second dielectric covers at least a portion of the grating structure such that the first and second dielectrics together define a photonic crystal having an optical resonance; and
    a Fabry-Perot optical cavity between the photonic crystal and the silicon substrate, wherein the Fabry-Perot optical cavity couples to the optical resonance of the photonic crystal.

2. The photonic crystal structure of claim 1, wherein the first dielectric comprises silicon oxide.

3. The photonic crystal structure of claim 1, wherein the second dielectric comprises titanium oxide.

4. The photonic crystal structure of claim 1, further comprising one or more intermediate layers between the silicon substrate and the first surface of the first dielectric.

5. The photonic crystal structure of claim 4, wherein the one or more intermediate layers define the Fabry-Perot optical cavity between the photonic crystal and the silicon substrate.

6. The photonic crystal structure of claim 5, wherein the one or more intermediate layers includes a reflective metal layer on the silicon substrate.

7. The photonic crystal structure of claim 1, further comprising a fluorophore coupled to the photonic crystal, wherein the fluorophore is configured to emit fluorescence radiation at an emission wavelength at an emission angle in response to receiving excitation radiation at an excitation wavelength at an excitation angle.

8. The photonic crystal structure of claim 7, wherein the optical resonance of the photonic crystal has a resonance wavelength at the excitation angle that corresponds to the excitation wavelength of the fluorophore.

9. The photonic crystal structure of claim 7, wherein the optical resonance of the photonic crystal has a resonance wavelength at the emission angle that corresponds to the emission wavelength of the fluorophore.

10. A method, comprising:
    exposing a functionalized photonic crystal structure to a sample to provide a sample-exposed photonic crystal structure, wherein the functionalized photonic crystal structure comprises a silicon substrate, a photonic crystal having an optical resonance, a Fabry-Perot optical cavity between the photonic crystal and the silicon substrate, wherein the Fabry-Perot optical cavity couples to the optical resonance of the photonic crystal, and a capture ligand coupled to a surface of the photonic crystal, wherein the capture ligand is configured to bind to a target in the sample to form a fluorescent complex, wherein the fluorescent complex comprises a fluorophore configured to emit fluorescence radiation at an emission wavelength in response to receiving excitation radiation at an excitation wavelength;

exposing the sample-exposed photonic crystal structure to incident light from a light source at an angle of incidence, wherein the incident light includes light at the excitation wavelength; and detecting, by a detector, fluorescence radiation emitted from the fluorescent complex at an emission angle in response to the incident light from the light source.

11. The method of claim 10, wherein the capture ligand comprises an antibody or an oligonucleotide.

12. The method of 10, wherein a plurality of different capture ligands are bound to the surface of the photonic crystal at a plurality of discrete locations such that each capture ligand is configured to bind to a respective target in the sample to form a respective fluorescent complex, further comprising:

sequentially exposing each discrete location in the sample-exposed photonic crystal structure to incident light from the light source at the angle of incidence; and sequentially detecting, by the detector, fluorescence radiation emitted at the emission angle from each respective fluorescent complex in each discrete location.

13. The method of claim 10, wherein the optical resonance of the photonic crystal has a resonance wavelength at the angle of incidence that corresponds to the excitation wavelength of the fluorophore.

14. The method of claim 10, wherein the optical resonance of the photonic crystal has a resonance wavelength at the emission angle that corresponds to the emission wavelength of the fluorophore.

15. The method of claim 10, wherein the fluorophore is present in the functionalized photonic crystal structure prior to exposing the functionalized photonic crystal structure to the sample.

16. The method of claim 10, wherein the fluorophore is present in the sample prior to exposing the functionalized photonic crystal structure to the sample.

17. The method of claim 10, wherein the photonic crystal comprises a grating structure having a grating direction, and wherein the incident light from the light source is focused to a focal line on the surface of the photonic crystal such that the focal line is substantially parallel to the grating direction.

18. The method of claim 17, wherein the light from the light source is collimated at the focal line in a direction substantially perpendicular to the grating direction.

19. An instrument for exciting a fluorophore coupled to a surface of a photonic crystal having an optical resonance, wherein the fluorophore is configured to emit fluorescence radiation at an emission wavelength in response to receiving excitation radiation at an excitation wavelength, and wherein the photonic crystal comprises a grating structure having a grating direction, the instrument comprising:

a light source, wherein the light source is configured to emit incident light that includes light at the excitation wavelength of the fluorophore;

a collimator for collimating the incident light from the light source to provide collimated incident light;

a focusing system for directing the collimated incident light onto the surface of the photonic crystal at an angle of incidence and for focusing the collimated incident light to a focal line on the surface of the photonic crystal such that the focal line is substantially parallel to the grating direction and the collimated incident light at the focal line is collimated in a direction substantially perpendicular to the grating direction; and a detection system configured to detect fluorescence radiation emitted by the fluorophore at an emission angle in response to the collimated incident light directed onto the surface of the photonic crystal.

20. The instrument of claim 19, wherein the optical resonance has a resonance wavelength at the angle of incidence that corresponds to the excitation wavelength of the fluorophore.

21. The instrument of claim 19, wherein the optical resonance has a resonance wavelength at the emission angle that corresponds to the emission wavelength of the fluorophore.

22. The instrument of claim 19, wherein the detection system comprises a CCD camera and a filter, wherein the filter is configured to pass light at the emission wavelength and block light at the excitation wavelength.

23. The instrument of claim 19, wherein the focusing system comprises a cylindrical lens and an objective lens, wherein the cylindrical lens has a cylindrical-lens focus at a location in a focal plane of the objective lens, and wherein the location of the cylindrical-lens focus in the focal plane of the objective lens defines the angle of incidence.

24. The instrument of claim 23, wherein the objective lens is configured to collect fluorescence radiation emitted from the focal line on the photonic crystal and to direct the collected fluorescence radiation toward the detection system.

25. The instrument of claim 24, wherein the focusing system comprises a dichroic mirror configured to reflect light at the excitation wavelength and to transmit light at the emission wavelength, and wherein the objective lens is configured to direct the collected fluorescence radiation toward the detection system through the dichroic mirror.

26. The instrument of claim 24, wherein the fluorophore is coupled to the surface of the photonic crystal at a plurality of discrete locations, and wherein the instrument comprises a movable stage for moving the photonic crystal relative to the objective lens such that each of the discrete locations is exposed to the collimated incident light and the objective lens collects fluorescence radiation emitted from each of the discrete locations and directs the fluorescence radiation collected from each of the discrete locations toward the detection system.

* * * * *